United States Patent [19]

Lux et al.

[11] Patent Number: 5,262,031
[45] Date of Patent: Nov. 16, 1993

[54] ELECTROOSMOTIC FLOW CONTROL APPARATUS FOR CAPILLARY ELECTROPHORESIS

[75] Inventors: Jurgen A. Lux, Niederkirchen; Sally A. Swedberg, Waldbronn; James E. Young, La Honda; Douglass McManigill, Palo Alto, both of Calif.

[73] Assignee: Hewlett-Packard Company, Palo Alto, Calif.

[21] Appl. No.: 834,174

[22] Filed: Feb. 7, 1992

Related U.S. Application Data

[63] Continuation-in-part of Ser. No. 754,797, Sep. 4, 1991, Pat. No. 5,180,475, and a continuation-in-part of Ser. No. 718,600, Jun. 21, 1991, abandoned.

[51] Int. Cl.⁵ .................... G01N 27/26; G01N 27/447
[52] U.S. Cl. .................... 204/299; 204/180.1
[58] Field of Search .................... 204/180.1, 299 R

[56] References Cited

U.S. PATENT DOCUMENTS 5,151,164 9/1992 Blanchard et al. ............ 204/299 R

Primary Examiner—John Niebling
Assistant Examiner—John S. Starsiak, Jr.

[57] ABSTRACT

An electrophoretic apparatus that is useful for separation of analytes, such as proteins, comprises a capillary tube that has an interfacial layer bonded to reduce interactions between the bore and analytes during electroosmotic flow through the capillary, and an electrically modified media carried by or contacting a capillary wall outward from the bore. The modified media can be an electrically resistive coating or an electrically conductive coating. Together with appropriate power supply configurations, the electrically modified media permits the application of a voltage gradient that is transverse to the electrophoretic gradient, and provides electroosmotic flow control in cooperation with the interfacial layer.

10 Claims, 3 Drawing Sheets

ELECTROOSMOTIC FLOW CONTROL APPARATUS FOR CAPILLARY ELECTROPHORESIS

This application is a continuation-in-part of Ser. No. 07/754,797, filed Sep. 4, 1991, now U.S. Pat. No. 5,180,475, inventors Young et al., of common assignment herewith and of Ser. No. 07/718,600, filed Jun. 21, 1991, now abandoned, inventors Swedberg and McManigill, also of common assignment herewith.

FIELD OF THE INVENTION

The present invention generally relates to the separation of analytes by capillary zone electrophoresis, and particularly to systems permitting control of the electroosmotic flow.

BACKGROUND OF THE INVENTION

High Resolution Capillary Electrophoresis ("HRCE") in small bore capillaries (such as less than or to 75 $\mu$) was first demonstrated by Jorgenson and Lukacs, and has proven useful as an efficient method for the separation of small solutes. *J. Chromatog.*, 218 (1981), page 209; *Anal. Chem.*, 53 (1981), page 1298.

Attractive factors for electrophoretic separations by capillary zone electrophoresis are the small sample sizes, little or no sample pretreatment, and the potential for quantification and recovery of biologically active samples. The separation process is strongly influenced by an electroosmosis effect, generally described as the flow of a liquid in contact with a solid surface under the influence of a tangentially applied electric field. Electroosmotic flow ("EOF") and differences in electrophoretic mobilities combine to provide a spatial separation of constituents of the sample solution at the outlet end of the capillary tube.

Electrophoretic migration is the movement of charged constituents in response to an electric field. A positively charged molecule will migrate towards the cathode, while a negatively charged molecule will migrate towards the anode. The net movement of the charged species in the separation chamber is then governed by the vector sum of the electrophoretic mobility ("EPM") and the electroosmotic flow ("EOF"), given by:

$$\mu \text{ total} = EOF + \mu \ EPM$$

It is apparent from this expression that if the EOF is greater than the electrophoretic mobility of a species migrating against the flow, then the net migration of the species will be in the direction of the EOF. Consequently, electroosmotic flow is a high efficiency mass transport means for moving neutral and oppositely charged constituents of a sample past a single point of detection.

For open tubular electrophoresis, it is necessary to have control over the EOF in order to optimize resolution and analysis time. Many experimental conditions, such as surface modification, field strength, buffer pH, ionic strength and species and organic modifiers such as solvents or surfactants, may alter EOF. Currently, in order to attempt to optimize separation parameters, practitioners have had systematically to vary the different conditions in attempts to optimize separations.

After a decade of intense interest and development in open tubular capillary electrophoresis as an analytical technique, fused silica (usually externally coated with polyamide) has been the capillary tubing of choice. As a high energy surface, its greatest single weakness is its affinity for a wide variety of solutes of interest. The untoward solute/surface interactions are a major source of loss of efficiency and reproducibility in this evolving separation technique. Numerous attempts at surface deactivation have been reported, ranging from dynamic deactivation using additives in the electrophoresis solution to specific chemical modification of the silica surface. All deactivation techniques ultimately have an impact on the EOF.

U.S. Pat. No. 4,680,201, issued 1987, inventor Hjerten, describes a method for preparing a thin wall capillary tube for electrophoretic separations by use of a bifunctional compound in which one group (usually a terminal—$SiX_3$ group where X=ethoxy, methoxy or chloride) reacts with the glass wall and the other (usually an olefin group) does so with a monomer taking part in a polymerization process. This process is said to result in a wall-bonded, polymer-coated capillary useful for open tubular electrophoresis.

U.S. Pat. No. 4,931,328, inventor Swedberg, issued Jun. 5, 1990, describes a modified capillary tube that has an interfacial layer covalently bonded to the inner wall of the capillary tube. The interfacial layer is effective to reduce interactions between the inner wall and protein solutes, and includes a hydratable amphoteric phase. This amphoteric phase has a determinable isoelectric point and permits electroosmotic flow control by selection of solution pH.

U.S. Pat. No. 5,006,313, issued Apr. 9, 1991, inventor Swedberg, describes capillary tubes with a reduced interaction phase coated along the bore for reducing interactions of protein solutes with the surface. When this interfacial layer is about 4 to about 6 molecular layers thick, then it has been found that electroosmotic flow is reasonably high in use for capillary zone electrophoresis.

Lee et al., *Anal. Chem.*, 62 (1990), pages 1550-1552, reported a technique in which capillary electroosmosis with bare fused silica had an external electric field applied to modify the zeta potential at the aqueous/inner capillary interface. That is, this technique factorially couples externally applied potential with the potential across the buffer solution inside the capillary. This electric potential gradient across the capillary wall vectorially sums with the polarity and magnitude of the charged double ion layer at the surface/liquid interface of the interior surface of the capillary, which is the so called "zeta potential". The resultant direction and flow rate of electroosmosis is dependent upon the combination of the external transverse field and the zeta potential polarity and the zeta potential magnitude.

Despite the advances, current HRCE column technology generally suffers from two major disadvantages: lack of ability to vary the EOF component when flow control is retained, independent of the electrophoretic mobility of solute species of interest; and, undesirable solute/surface interactions. The former disadvantage greatly limits the ability to optimize separation conditions and analysis time and the latter degrades the reproducibility and efficiency of the separation technique.

SUMMARY OF THE INVENTION

In one aspect of this invention, an electrophoretic apparatus that is useful for separation of analytes comprises a capillary tube having reduced analyte interaction and a means for applying a voltage gradient. The capillary tube defines a bore and an outward wall. The bore forms a pathway upon which an electrophoretic gradient can be imposed between an upstream position and a downstream position of the pathway. The bore has an interfacial layer that is bonded or highly physisorbed, which is effective to reduce interactions with analytes during electroosmotic flow along the pathway. The applying means permits application of a voltage gradient that is transverse with respect to the electrophoretic gradient which, when summed with the potential at the interfacial layer, permits electroosmotic flow control (e.g., provides the ability to vary the EOF component).

In one embodiment, the applying means includes an electrically resistive media in electrical communication exterior the surface of the capillary and longitudinally spaced power supplies are used to apply a voltage gradient to the wall. This electrically resistive media can take the form of a resistive coating on the wall, or a resistive fluid surrounding the wall. In another embodiment of the applying means, an electrically conductive coating is on the capillary outer wall, which is grounded and also may be held at some constant potential.

Use of the inventive electrophoretic apparatus affords unique control over the EOF, extends the pH range of analysis, and provides highly efficient separations.

DETAILED DESCRIPTION OF THE PREFERRED EMBODIMENTS

Figure 1:
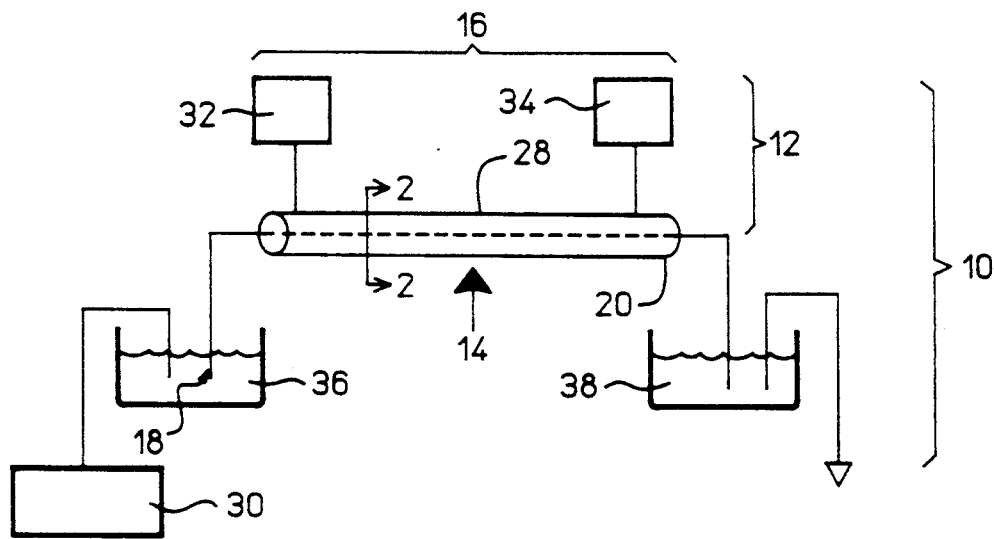
FIG. 1 is a schematic view of one electrophoresis embodiment for controlling electroosmotic flow.

With reference to FIG. 1, an electrophoretic system 10 is shown, where an electrophoretic apparatus 12 includes a capillary tube 14 and a means 16 for applying a voltage gradient transverse to the longitudinal axis of capillary tube 14. Use of applying means 16 during analyte separation will sometimes be referred to as the "voltage offset method." Capillary tube 14 generally longitudinally extends between an inlet end 18 and an outlet end 20.

Figure 2:
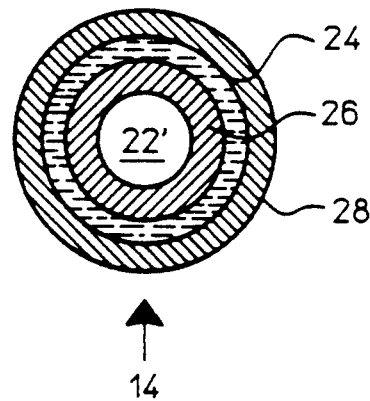
FIG. 2 is a cross-sectional view, taken along line II—II of FIG. 1.

With reference to FIG. 2, capillary tube 14 defines a bore 22 and a wall 24 outward from, such as concentric with, bore 22. Bore 22 forms a pathway along which analytes are separated when an electrophoretic gradient is imposed between inlet, or pathway upstream position, 18 and outlet, or pathway downstream position, 20. Bore 14 carries an interfacial layer 26 that is effective to reduce interactions between the bore 22 and analytes being separated during electroosmotic flow along the pathway. Layer 26 can be chemically bonded or highly physisorbed to bore 22, and is stable under capillary separation conditions. Layer 26 functions to deactivate the bore surface and, together with applying means 16, permits control over the EOF. Suitable materials for forming interfacial layer 26 include hydratable amphoteric phases, an ionizable species having a basic or an acidic equilibrium or electrically neutral species such as polymers (e.g., polymethylsiloxane).

Briefly, the interfacial layer is interposed between the bore of the capillary and the protein solutions when in use. The reduced interaction phase of such coating is effective to reduce interactions between analytes, such as protein solutes, and the bore, preferably while permitting reasonably high electroosmotic flow When this interfacial layer is chemically bonded and is about four to about six molecular layers thick, then it has been found that electroosmotic flow is reasonably high in use for capillary zone electrophoresis; however, fewer molecular layers (so long as at least one) or greater molecular layers are possible, and may be desirable for particular applications. Highly physisorbed interfacial layers are preferably from about 0.1 $\mu$m to about 2 $\mu$m in thickness.

Several embodiments useful for interfacial layer 26 are as described in U.S. Pat. No. 4,931,328, issued Jun. 5, 1990, which is incorporated in its entirety by reference herein. A first embodiment for the interfacial layer is where the reduced interaction phase includes an ionizable species having an acidic equilibrium or a basic equilibrium. An illustrative ionizable species with a basic equilibrium is an amino group. An illustrative ionizable species with an acidic equilibrium is a carboxyl group.

Preparation of both ionizable species types is as follows. When the capillary bore, or inner wall, surface to be modified is silica based, it is first hydrated and then reacted with an organo- or chlorosilane having two functional end groups. Concentrations of silylating reagent in aqueous solution from about 0.1 wt. % to about 1 wt. % result in about four to six molecular layers being bonded to the surface. These about four to six layers ensure there are no remaining unreacted silanol groups. The unreacted functional group of the silylating reagent is a nitrogen nucleophile or an oxygen nucleophile. The nitrogen nucleophile provides amino groups for ionizable species having a basic equilibrium. Alternatively, the nitrogen nucleophile may be converted to carboxyl groups, as further described hereinafter. The oxygen nucleophile (e.g., hydroxyl groups) may be converted to carboxyl groups as ionizable species having an acidic equilibrium, as further described hereinafter. However, other capillary materials than silica may be used. A wider range of materials, in addition to silica, can be modified so as to have reduced interactions with protein solutes. These additional materials are generally polymers, which can form the capillary tubing itself or can be coated on or bonded within a silica capillary wall. That is, when the polymers do not themselves form, or define, the capillary tube, then they are carried by the inner wall of the tube and the interfacial layer is further coated onto the polymer.

Among the suitable polymeric materials for forming capillaries are nylon, styrene or phenyl silicones, acrylics, polyurethanes, polycarbonates, polyesters, silicon alkoxy elastomers, and fluorocarbons. Although silica is a very high energy surface and the polymeric materials can provide a relatively lower energy surface, the polymeric surfaces still need to be modified to reduce protein interactions along the surface and to cooperate with applying means 16 for EOF control. These polymeric surfaces are modified to precursor surfaces. The precursor surfaces are then further preferably treated so as to add the interfacial layer.

The polymers used preferably provide multipoint attachments for the moieties that will form the interfacial layer when the layer is to be chemically bonded. Thus, for example, the polymeric surfaces may be modified to receive the interfacial layer by activating functional groups such as oxygen or nitrogen nucleophiles, but can also be a carbon electrophile. For example, if one desired to use styrene, then the multi-point attachments through which the interfacial layer can be bonded will normally be amine groups. One useful technique for preparing the functional amine groups is by perfusing the styrene surface with 47% nitric acid in sulfuric acid at 0° C. for 20 minutes at a flow rate of 1-2 column volumes per minute. The capillary is then flushed with water and reduction accomplished (such as with 6% $Na_2S_2O_4$ in 2 M sodium hydroxide). If one chooses nylon as the polymeric material, then the nylon surface may be prepared by perfusing 4 N hydrochloric acid, flushing with deionized water. Additional examples are given in U.S. Pat. application Ser. No. 07/507,937, filed Apr. 11, 1990, inventor Swedberg, of common assignment herewith Another embodiment of capillary tubes with an interfacial layer are where a hydratable amphoteric phase is prepared by reacting (that is, covalently bonding, or coupling) a protein, peptide, or an ampholyte with the oxygen or nitrogen nucleophiles as previously described. The amino groups (of the nitrogen nucleophile) and the carboxyl or hydroxy groups (of the oxygen nucleophile) are activated to effect the coupling. For example, the amino groups may be activated with glutaraldehyde or carbonyldiimidazole, and the carboxyl or hydroxy groups with carbonyldiimidazole. Alternatively, the proteins, peptides, and ampholytes themselves may be activated to effect the coupling. For example, dipeptides may be activated with glutaraldehyde while other, larger chain peptides and ampholytes may be activated with carbodiimide.

Suitable proteins, peptides, and ampholytes for inclusion in the covalently bound interfacial typically layer have a molecular weight between about 200 daltons to about 58,000 daltons. That is, molecules in size from dipeptides to macromolecules can be utilized. Ampholytes are particularly preferred because these synthetic molecules are commercially available for particular, narrow pH ranges. As is known, ampholytes may be synthesized by copolymerization of amines and amino acids with epichlorohydrin. By a suitable choice of amines and amino acids, a large part of the buffer capacity can be concentrated into a narrow pH-interval (2-3 pH units). Ampholytes are commercially available from sources such as Pharmacia Fine Chemicals (under the trade name "Pharmalyte") and from Bio-Rad Laboratories (under the trade name "Bio-Lyte").

The amphoteric phase, whether protein, peptide, or ampholyte, includes ionizable cationic and ionizable anionic species. The cationic species include amino, guanidinium, imidazolium, and mixtures thereof. Amino species for the cationic species may be obtained from lysine side chains, guanidiminium may be obtained from arginine side chains, and imidiazolium from histidine. The anionic species of the amphoteric phase has carboxyl groups from aspartic acid and glutamic acid side chains. The synthetic ampholytes have ionizable cationic species from amino groups, most of which are tertiary, but a few being secondary or primary. The anionic species is provided by carboxyl groups of two kinds: $\alpha$-amino carboxylic groups and carboxyl groups from polymerized glycylglycin.

The proteins, peptides, and ampholytes suitable for forming the amphoteric phase are all highly hydrated under use conditions. This is important for reversibility of interactions (albeit reduced) between the coated surface and the protein solutes.

The point of zero charge ("PZC") is generally defined as the pH at which the net charge of a surface is zero. Interfacial layer 26 is prepared so as to provide a variety of surfaces with unique PZC characteristics, and preferably the point of zero charge will be at or near the desired pH of the solution filling bore 22.

The analytes to be separated include proteins. For protein separations it is particularly desirable to choose specific pH conditions under which the separations will be done. In addition, certain additives in the buffer solution may strongly influence the zeta potential, such as detergents (e.g. SDS) or heavy metal ions (e.g. barium).

We have surprisingly discovered that electrically neutral coatings can also be used to practice the invention. Neutral polymers may interact with the buffer solution itself through hydrophilic, hydrophobic, pi-pi, hydrogen bonding, dipole-dipole, or induced dipole interactions. Different combinations and strengths of these interactions may cause different amounts of electroosmotic flow control when practicing the invention with electrically neutral coatings. It is possible that electrically neutral coatings might function through ion absorption or perhaps through an induced dipole action, but the invention is not limited to such theories. Our particularly preferred embodiment for practicing the invention uses polymethylsiloxane as a highly physisorbed coating on the capillary bore. Another useful electrically neutral coating is N-butyltrimethoxysilane, which we have chemically bonded to the bore by standard silylating techniques.

Capillary tube 14 has outer wall 24 in electrical communication with a media 28 that is electrically modified and forms a part of applying means 16, as will now be described by illustration with several embodiments.

Returning to FIG. 1, one embodiment has a plurality of power supplies 30, 32, and 34, which are used to practice the voltage offset method. Power supply 30 is used to impose the electrophoretic gradient between bore 14, inlet 18 and outlet 20; however, power supplies 32, 34 each permit application of a voltage gradient that is transverse with respect to the electrophoretic gradient established by power supply 30. The voltages applied by each of power supplies 32, 34 differ from one another so that the transversely applied field is as a voltage gradient. It should be understood, however, that a unitary power supply could be used rather than the two power supplies 32, 34, where such a unitary power supply (not illustrated) has a resistor (ladder) so that one could select different voltages and apply the voltage gradient necessary to practice this voltage offset method.

In the FIG. 1 embodiment, the media 28 is electrically resistive (and in electrical communication with outer wall 24). Suitable electrically resistive media are where outer wall 24 carries media 28 as a resistive coating. An alternative embodiment is where media 28 is a resistive liquid surrounding outer wall 24.

One illustrative resistive coating is comprised of a polymer containing particles of carbon black. A particularly preferred bulk resistivity is about 2 kOhms/cm. About 7.5 wt. % carbon black in polyimide provides such a desired resistivity, which, of course, can be adjusted by adjusting the proportion of carbon black. A preferred sheet resistance of about 800 kOhms can also be adjusted by the number of coatings applied. Example 1 illustrates preparation of a capillary with an electrically resistive coating.

EXAMPLE 1

A slurry was prepared containing 2.00 g polyimide (AMOCO 7501) and 150 mg of carbon black (Cabot; Mogul L, GP-3187) in 20 ml of 1-methyl-2-pyrrolidinone. These components were mixed in an ultrasonic bath for two hours. An aliquot of the slurry was sprayed onto a previously internally coated silica capillary, which was held in a fixture and rotated during spraying. Multi-layer coatings were achieved by evaporating solvent from the coating solution with a flow of hot air provided by a heat gun, and then spraying a second layer onto the capillary and repeating the drying step. The resistance achieved along the capillary exterior was measured with an ohm meter.

If the electrically resistive media 28 is to be achieved through a resistive liquid, then an outer jacket (not illustrated) can surround tube 14 and be filled with an appropriate buffer solution.

In performing an electrophoretic separation with apparatus 10, the inlet end 18 of capillary tube 14 will be in fluid communication with sample vial 36 (such as immersed in vial 36), while buffer reservoir vial 38 will be in a fluid communication with outlet end 20 of tube 14. The high voltage power supply 30 will be electrically connected to sample vial 36 via a power line, and power supply 30 will be operated to provide a high voltage.

The embodiment illustrated by FIG. 1 permits the application of transverse voltage gradient that also longitudinally extends over substantially the entire pathway. This means the entire transversely applied field is substantially uniform, and the zeta potential can be uniformly changed. Additional advantages of this embodiment include the application of high fields and the possibility of better EOF modulation.

Figure 3:
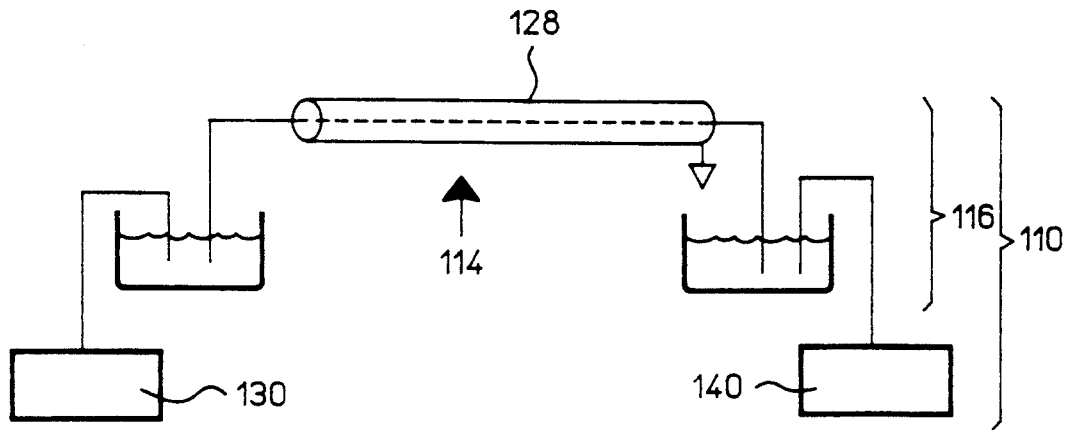
FIG. 3 is a schematic view of another electrophoresis system, embodiment of the invention.

Another embodiment, shown as electrophoretic apparatus 110, is illustrated by FIG. 3. Here, applying means 116 is accomplished when the tube 114 carries a conductive coating 128, which preferably is grounded (and thus provides a defined reference point to the voltage offset). Grounding is also believed to increase the zeta potential, and to reduce extraneous fringe fields present in the apparatus.

Suitable conductive coatings may be deposited by evaporation, spraying, sputtering, or the like processes. The conductive material itself may be any conductive metal (e.g., gold, silver, aluminum, nickel, etc.), a conductive polymer or a conductive metal oxide. Conductive coatings can be applied over the standard polyimide coatings placed on commercially available capillaries, or can be deposited on the bare capillary surface itself. The coating can be placed upon substantially the entire tube 114, or on whatever portion or portions of tube 114 are desired. An area that has been masked or (where the conductive coating material has been removed) can be provided to provide clear access to the bare capillary for the light path of a detector. A conductive bridge can be used to provide electrical connection across such an uncoated area of the capillary to allow for maximal electroosmotic flow control. Alternatively, detection can be outside of the EOF control zone.

In the embodiment illustrated by FIG. 3, the applying means 116 is further achieved with power supplies 130 and 140. That is, the voltage offset is applied to the buffer solution inside capillary 114 rather than by the application of a field external to the separation capillary (as illustrated by FIG. 1). An advantage of the FIG. 3 embodiment is that only two high voltage power supplies are needed. Compared to an ungrounded capillary (as the FIG. 1 embodiment), the zeta potential of the FIG. 3 embodiment can be increased, although the same voltage offset is applied. This higher zeta potential can lead to higher osmotic flow velocity, and the removal of exterior charges significantly reduces electrostatic effects, which provides a better UV signal and more uniform flow rates.

Example 2 illustrates a particularly preferred embodiment.

EXAMPLE 2

Five meter sections of bare fused silica capillaries (0.05 mm ID, 0.15 mm OD) were coated by filing the capillaries with a 0.1-1% solution of PMS oligomers (containing about 2% vinyl groups) in pentane under 5 bar nitrogen pressure with a small pressure bomb. The capillaries were closed after filling with a short section of a clamped heat shrink tubing. The solvent was then evaporated from one end by vacuum. During evaporation the capillaries were fixed in a thermostat controlled water bath. After the coating the capillaries were heated to 200° C. in a GC oven to crosslink the PMS coating. The residual PMS was then removed by several rinsing steps with pentane. The film thickness and performance were assessed with the Grob test in a GC experiment using 0.2 $\mu$l Grob test mixture (temperature progressed from 60° C. to 230° C. at 8° C./min, 2.5 bar hydrogen). The film thickness was determined to be 0.23 $\mu$m. Then the long capillaries were cut to desired lengths (such as, for example, 40 cm) for performing electrophoresis.

A capillary tube having a PMS (polymethylsiloxane) internal coating, prepared in a manner analogous to that just described, was externally coated by painting a polymer containing nickel onto the capillary. Thus, a commercially available composition (typically used to touch-up or repair printed circuit boards) available from GC Electronics under the name "Nickel-Print" (including a polymer solution in a fast drying solvent and containing a high concentration of conductive nickel powder) was painted onto the capillary exterior using an art brush. The coating dries quickly and is tested for high conductivity with an ohm meter.

Figure 4:
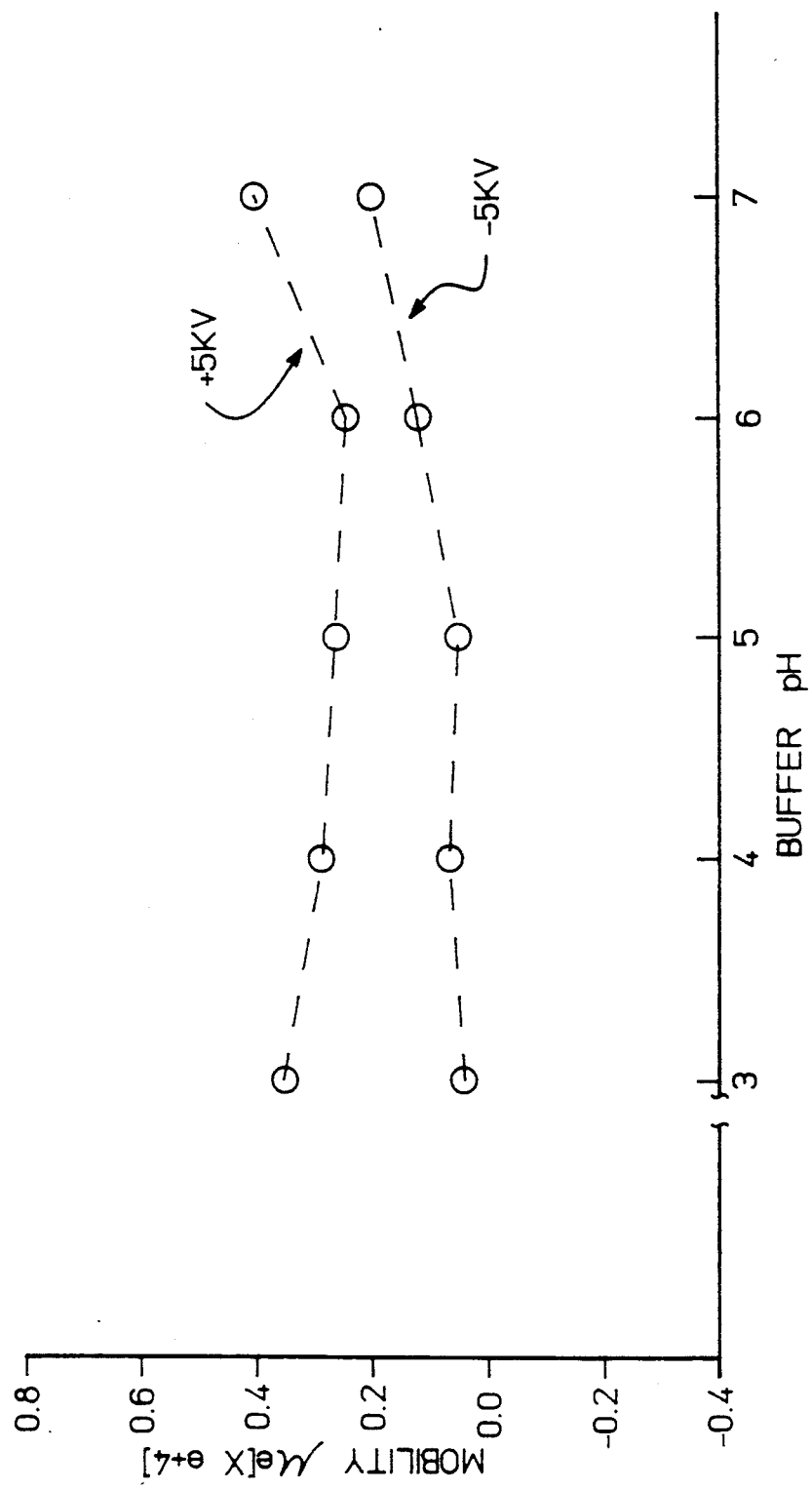
FIG. 4 graphically illustrates use of an embodiment of the invention to control EOF over a wide pH range at two different control voltages.

This internally and externally modified silica capillary was then assembled as illustrated by FIG. 3, and was run with citrate buffer using two different control (offset) voltages. There was 10 kV over 40 cm overall length, and a distance of 16.5 cm to the detector. Citrate buffer (10 mM) with 0.1% DMSO was used for the sample fluid to determine EOF controllability. In order to prepare the different pH points, a constant molarity of 10 mM was used, but ionic strength was varied by titrating to the desired pH point with sodium citrate. With reference to FIG. 4, the inventive embodiment was run at a voltage offset of +5 kV in one experiment and at a voltage offset of −5 kV in another. As shown by the plotted data, substantially uniform EOF control was achieved in both runs over a pH range from 3 to 7.

In other experiments (with an internal coating from chemically bonded N-butyltrimethoxysilane of glycidoxypropyltrimethoxysilane), we have found that the interfacial layer and applying means 16, 116 permits EOF control, while solely using applying means 16, 116 itself (without the interfacial layer) does not, or solely using the inventive apparatus but without application of the transverse gradient can result in inferior separations.

EXAMPLE 3

Figure 5:
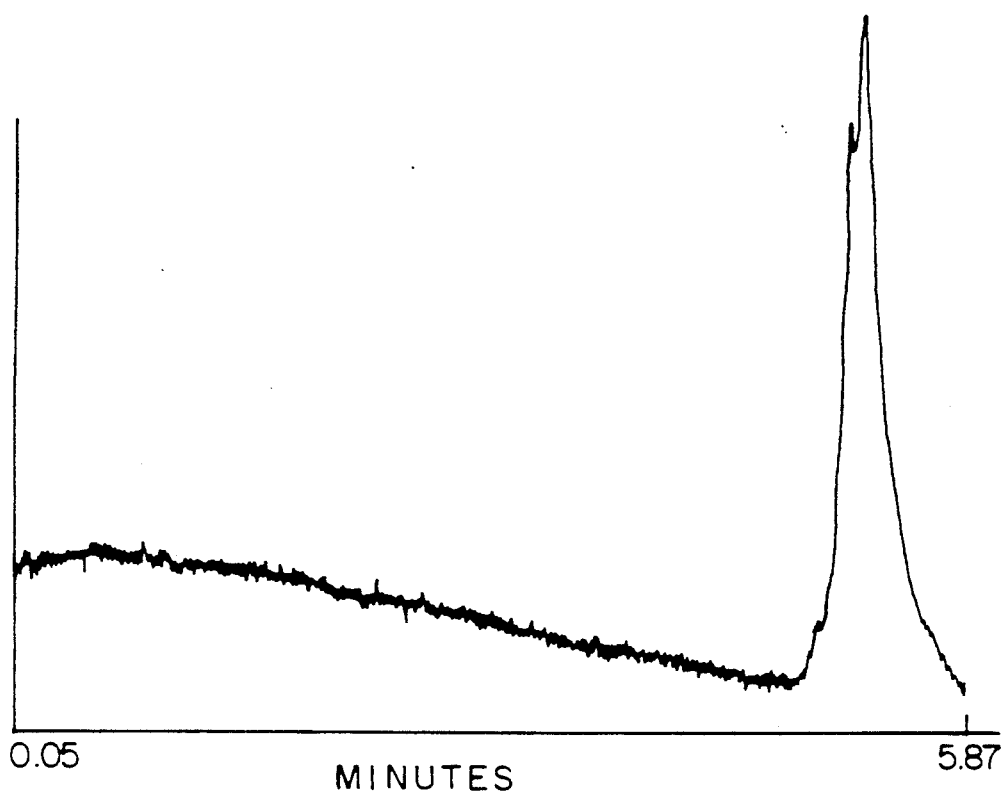
FIG. 5 illustrates an electropherogram of a protein mixture passed through an apparatus embodiment of the invention.
Figure 6:
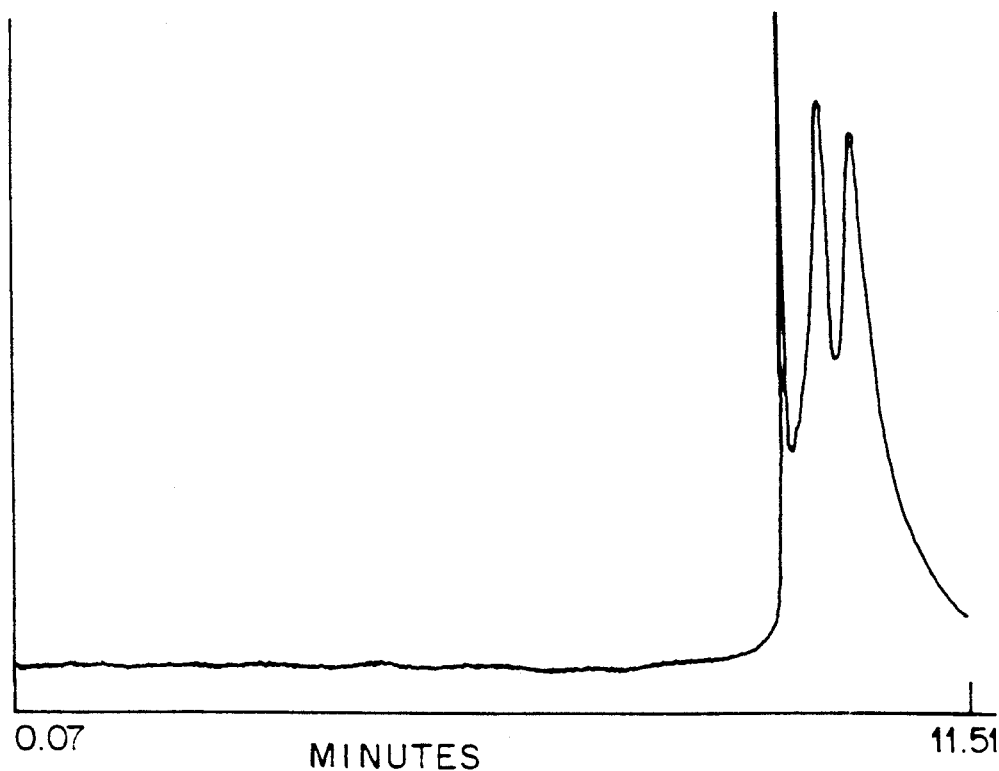
FIG. 6 is an electropherogram of the same protein mixture in the same apparatus as for FIG. 5, except there has been a significant transverse gradient (magnitude change) applied in accordance with the invention.

The electropherograms illustrated by FIGS. 5 and 6 were obtained from the following experiment. Both were run in the same inventive apparatus. Column dimensions were 50 $\mu$ ID, 187 $\mu$ OD, 40 cm total length, and 23 cm to the detector. The exterior of the capillary had a conductive nickel coating and was grounded, as illustrated by the FIG. 3 embodiment. The interior interfacial layer was formed from glycidoxypropyltrimethoxysilane (0.5% v/v solution), by pumping this solution through the capillary at a rate of about 1–2 $\mu$l/min for 1 hour in one direction, then pumping in the opposite direction for another hour, and curing overnight with a flowing stream of helium. The buffer used for the separation was 10 mM OAc at pH 5 plus 18 mM CHAPSO (surfactant). The analyte was delipidized bacteriorhodopsin (dBR) in the buffer at 1 mg/ml. Detection was on-column at 210 nm. The sample was applied by injection: electroosmotic −3 sec at 50 V/cm. The electropherogram trace of the sample as a function of minutes was as shown by FIG. 5. The axial field was +250 V/cm (cathode 0, anode +10 kV). However, when the experiment was repeated with the same inventive apparatus, same buffer, and same sample, and run as just described except that in addition to the applied axial field there was applied a transverse gradient across the capillary wall by virtue of the following voltages—cathode −20 kV, anode −10 kV—then the electropherogram with three distinct peaks was obtained as shown by FIG. 6.

It is to be understood that while the invention has been described above in conjunction with preferred specific embodiments, the description and examples are intended to illustrate and not limit the scope of the invention, which is defined by the scope of the appended claims.

We claim:

1. An electrophoretic apparatus, useful for separation of analytes, comprising:
   a capillary tube defining a bore and a wall outward therefrom, the bore forming a pathway upon which a first directional electrophoretic gradient can be imposed between an upstream position and a downstream position of the pathway, the bore having an interfacial layer chemically bonded to or highly physisorbed thereon, being effective to reduce interactions between the bore and analytes during electroosmotic flow along the pathway and having a selected point of zero charge at or near the desired pH of solution in which analytes are carried; and
   means for applying a voltage gradient transverse with respect to the first directional electrophoretic gradient, the transverse voltage gradient and the interfacial layer together providing electroosmotic flow control.

2. The electrophoretic apparatus as in claim 1 wherein the applying means applies the transverse voltage gradient between the wall and the bore and longitudinally extends for at least part of the pathway.

3. The electrophoretic apparatus as in claim 1 wherein the applying means includes an electrically resistive media in electrical communication with the wall.

4. The electrophoretic apparatus as in claim 3 wherein the electrically resistive media includes a resistive coating on the wall or a resistive liquid surrounding the wall or combinations thereof.

5. The electrophoretic apparatus as in claim 1 wherein the applying means includes an electrically conductive coating on at least a portion of the wall.

6. The electrophoretic apparatus as in claim 1 wherein the interfacial layer is substantially electrically neutral, is a hydratable amphoteric phase or is an ionizable species having a basic or an acidic equilibrium.

7. The electrophoretic apparatus as in claim 1 wherein the interfacial layer is an electrically neutral polymer and the applying means includes an electrically conductive coating on the capillary wall.

8. The electrophoretic apparatus as in claim 7 wherein the capillary wall is grounded.

9. The electrophoretic apparatus as in claim 1 wherein in the interfacial layer is an hydratable amphoteric phase.

10. The electrophoretic apparatus as in claim 1 wherein the interfacial layer is an ionizable species having a basic or acidic equilibrium.

* * * * *